United States Patent [19]
Murphy

[11] Patent Number: 5,277,773
[45] Date of Patent: * Jan. 11, 1994

[54] CONVERSION OF HYDROCARBONS USING MICROWAVE RADIATION

[75] Inventor: William J. Murphy, Brights Grove, Canada

[73] Assignee: Exxon Research & Engineering Co., Florham Park, N.J.

[*] Notice: The portion of the term of this patent subsequent to Dec. 4, 2007 has been disclaimed.

[21] Appl. No.: 985,787

[22] Filed: Dec. 4, 1992

Related U.S. Application Data

[63] Continuation-in-part of Ser. No. 858,917, Mar. 27, 1992, Pat. No. 5,205,912, which is a continuation of Ser. No. 686,333, Apr. 16, 1991, abandoned, which is a continuation of Ser. No. 457,426, Dec. 27, 1989, abandoned.

[51] Int. Cl.$^5$ .............................. C07C 4/00
[52] U.S. Cl. ........................ 204/168; 204/157.43; 204/157.47; 204/157.52; 204/170; 204/156
[58] Field of Search ............ 204/157.43, 157.47, 204/157.6, 168, 170, 156, 157.52

[56] References Cited

U.S. PATENT DOCUMENTS

| | | | |
|---|---|---|---|
| 2,986,505 | 5/1958 | Lauer et al. | 204/156 |
| 3,320,146 | 5/1967 | Neely, Jr. | 204/168 |
| 3,328,276 | 6/1967 | Schmidt et al. | 204/170 |
| 3,663,394 | 5/1972 | Kawahara | 204/168 |
| 4,234,402 | 11/1980 | Kirkbride | 204/162 |
| 4,279,722 | 7/1981 | Kirkbride | 204/162 |
| 4,474,625 | 10/1984 | Cohen et al. | 148/1.5 |
| 4,574,038 | 3/1986 | Wan | 204/162 |
| 4,721,828 | 1/1988 | Withers | 585/500 |
| 4,919,974 | 4/1990 | McCune et al. | 427/249 |
| 4,975,164 | 12/1990 | Ravella et al. | 204/157.43 |
| 5,015,349 | 5/1991 | Suib et al. | 204/168 |

OTHER PUBLICATIONS

Sax and Lewis, Sr. *Hawley's Condensed Chemical Dictionary*, Van Nostrand Reinhold Co. New York: 1987, p. 1232.

Gasner et al., "Microwave and conventional pyrolysis of a bituminous coal", Chemical Abstracts 106: 7281h (1987).

Tanaka et al., "A Stoicheiometric Conversion of $CO_2 + CH_4$ into $2\ CO + 2\ H_2$ by Microwave Discharge", J. Chem. Soc., Chem. Commun., pp. 921-922 (1982).

*Primary Examiner*—John Niebling
*Assistant Examiner*—C. Delacroix-Muirheid
*Attorney, Agent, or Firm*—James H. Takemoto

[57] ABSTRACT

$C_{1+}$ hydrocarbons can be effectively converted to primarily unsaturated hydrocarbon and hydrogen by subjecting the $C_{1+}$ hydrocarbon to microwave radiation in the presence of water and at least one plasma initiator that is capable of initiating an electric discharge in an electromagnetic field.

13 Claims, 6 Drawing Sheets

CONVERSION OF HYDROCARBONS USING MICROWAVE RADIATION

This is a continuation in part of U.S. Ser. No. 858,917, now U.S. Pat. No. 5,205,912 filed Mar. 27, 1992, which is a Rule 60 Continuation of U.S. Ser. No. 686,333 filed Apr. 16, 1991, now abandoned, which is based on a Rule 60 Continuation of U.S. Ser. No. 457,426 filed Dec. 27, 1989, now abandoned, which is based on P.M. 87-SM-001B.

BACKGROUND OF THE INVENTION

1. Field of the Invention

This invention relates to a method for converting $C_{1+}$ hydrocarbons to primarily unsaturated hydrocarbons and hydrogen in the presence of water using microwave radiation.

2. Description of Related Art

Microwave energy has been used to convert methane to other hydrocarbons. For example, U.S. Pat. No. 4,574,038 discloses that methane can be converted to ethylene and hydrogen in a batch process at pressures of from 0.3 to 1 atmosphere by subjecting the methane to microwave radiation in the presence of a metal powder catalyst. Another example of methane conversion using microwave energy is U.S. Pat. No. 3,663,394. U.S. Pat. No. 4,975,164 discloses the conversion of $C_{2+}$ hydrocarbons to primarily unsaturated hydrocarbons and hydrogen using microwave radiation.

However, these patents do not suggest the particular hydrocarbon conversion process described below.

SUMMARY OF THE INVENTION

This invention concerns a method for converting $C_{1+}$ hydrocarbons to primarily unsaturated hydrocarbons and hydrogen which comprises:

(a) introducing into a reaction zone containing at least one plasma initiator capable of initiating an electric discharge in an electromagnetic field, a feed stream wherein the feed stream contains
  (1) at least one $C_{1+}$ hydrocarbon, and
  (2) from about 0.02 to about 20 wt. % water, based on the feed stream, and (b) subjecting the reaction zone to microwave radiation for a period of time sufficient to convert at least a portion of the $C_{1+}$ hydrocarbon to primarily unsaturated hydrocarbons and hydrogen. In a preferred embodiment, molecular hydrogen will be present in the feed stream and the plasma initiator will comprise a plurality of elongated metal wire segments arranged in close proximity to one another.

DETAILED DESCRIPTION OF THE INVENTION

Figure 1:
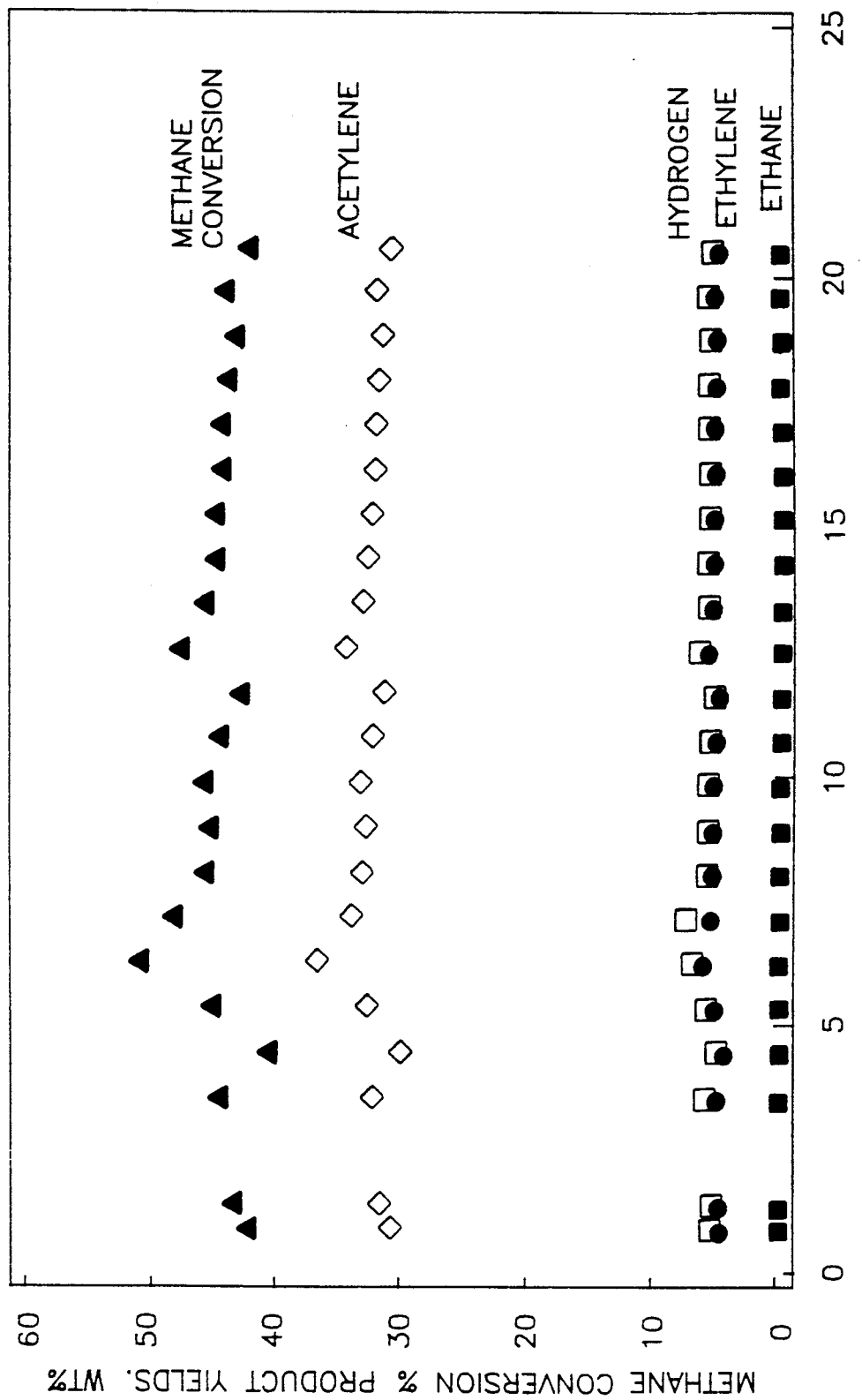
FIG. 1 is a graph of methane conversion and product yields versus time.

This invention requires the presence of a $C_{1+}$ hydrocarbon, water, at least one elongated plasma initiator capable of initiating an electric discharge in an electromagnetic field, and a source of microwave energy.

By initiating conversion of $C_{1+}$ hydrocarbons in the presence of water, it has been discovered the energy efficiency or rate of dissociation of the $C_{1+}$ hydrocarbon is substantially increased thereby increasing the overall conversion of $C_{1+}$ hydrocarbons into primarily unsaturated hydrocarbons and hydrogen. The amount of water necessary to enhance the conversion is from about 0.02 to about 20 wt. % based on feed, preferably about 0.1 to about 5 wt. %.

The products of the conversion reaction are primarily unsaturated $C_2-C_3$ hydrocarbons, e.g., acetylene, ethylene and propylene, with acetylene and ethylene the predominant components. Hydrogen is also a reaction product. Of the $C_{1+}$ hydrocarbons employed as reactants in the feed stream, methane is energetically the most difficult $C_{1+}$ hydrocarbon to convert. Other hydrocarbons such as ethane, butane and the like are more readily converted, and examples of such conversions in the absence of water are given in U.S. Pat. No. 4,975,164 which is incorporated herein by reference.

By "$C_{1+}$ hydrocarbon" is meant essentially any hydrocarbon containing at least one carbon atom that is in the vapor or gas phase at conversion conditions. The $C_{1+}$ hydrocarbons may be pure or mixtures. Examples of $C_{1+}$ hydrocarbons are methane, ethane, propane, butane, pentane, butenes, pentenes, light and heavy naphthas and distillates, gas oils kerosine and the like. Non-hydrocarbons (e.g., $H_2S$, $N_2$ and the like) may be present as well.

The plasma initiator may be essentially any material capable of accumulating an electric charge when placed in an electromagnetic field and then dissipating the charge (or initiating an electric discharge), for example, by ionizing a gas environment. This includes metal initiators, non-metal initiators (including semi-conductors), and composites of metal and non-metal initiators. As used herein, "composite" is meant to include mixtures (or combinations) of metals and non-metals. Examples of suitable metal initiators are tungsten, iron, nickel, copper, their alloys, or mixtures thereof. Preferred metal initiators are tungsten, iron, or mixtures thereof, with iron being particularly preferred. Examples of suitable non-metal initiators include carbon, alumina, manganese dioxide, magnetite, nickel oxide (e.g. NiO), iron oxide (e.g. $Fe_3O_4$), calcium aluminate, cobalt oxide, chromium nitride, iron sulfide (e.g. $FeS_2$, $Fe_{1-x}S$), copper sulfide (e.g.- $CUS_2$), or mixtures thereof. Calcium aluminate, carbon, iron oxide, or their mixtures are preferred non-metal initiators, with carbon being particularly preferred. Silica is not a suitable non-metal initiator. However, silica composited with a metal initiator or another non-metal initiator would be a suitable plasma initiator.

Although $C_{1+}$ hydrocarbon conversion can be effected using only one plasma initiator, conversion is enhanced if more than one (e.g., 6 or more) plasma initiators are used. Preferably, a plurality of plasma initiators are used. Most preferably, the plasma initiator will comprise a plurality of metal wire segments. Each plasma initiator should be of at least a minimum length that is sufficient to initiate an electric discharge when placed in an electromagnetic field. However, the precise minimum length of each initiator may vary with the frequency of the microwave source as well as the geometry of the reaction zone and of the initiator.

If more than one plasma initiator is used, a minimum distance should be maintained between each initiator to facilitate dissipation of the electric charge. However, the minimum distance will vary depending upon the frequency of the microwave source. As an example, the minimum distance should be at least about 0.25 cm, preferably at least about 0.5 cm, for a frequency of 2.45 GHz.

The plasma initiators should be elongated, but may be formed, combined, or bent in any convenient shape (e.g., straight, helix, spiral, and the like). Preferably, the initiators should be formed such that there are points or sharp edges at the ends or on the surface of the initiators.

The plasma initiators may be stationary within the reaction zone or they may be in motion. The motion can result from the initiators being fluidized by a feedstock gas or by other means (e.g. an external magnetic field gradient).

The frequency of the microwave source can vary broadly. Typically, the microwave energy will have a frequency of at least 0.3 GHz, with frequencies centered around 0.915, 2.45, 5.80, or 22.0 GHz presently being preferred in North America; particularly frequencies centered around 0.915, 2.45, or 5.80 GHz; especially frequencies centered around 0.915 or 2.45 GHz.

The microwave energy used in this invention may be pulsed or continuous. If pulsed, the duration of on-time pulses can vary broadly, but typically will range from about 1 nanosecond to about 20 seconds, preferably from about 1 millisecond to about 10 seconds, and most preferably from about 0.01 to about 0.2 seconds. The duration of off-time rests can vary broadly as well, but typically will range from about 1 nanosecond to about 100 seconds, preferably from about 0.003 to about 60 seconds, and most preferably from about 0.03 to about 5 seconds.

Molecular hydrogen should also be present in the reaction zone to maintain the activity of the plasma initiators for methane conversion. The amount of hydrogen in the reaction zone during conversion should be sufficient to maintain a mole ratio of methane to hydrogen greater than 1:1, preferably at least 1:1.5, more preferably at least 1:2, and most preferably at least 1:4. Although some methane conversion may occur at mole ratios of 1:1 or less, greater conversion will be obtained at higher mole ratios because hydrogen tends to reduce or inhibit the formation of carbonaceous deposits on the plasma initiators. While not wishing to be bound by any particular theory, it is believed that at lower mole ratios, greater amounts of carbonaceous deposits accumulate on the initiators and inhibit their ability to ionize the gas environment.

Although extraneous molecular hydrogen need not be added, if a sufficient amount of hydrogen is not present initially in the reaction zone, the initiators will deactivate until a sufficient amount of hydrogen is present (or has accumulated, for example, by recycling the hydrogen formed during conversion) to retard deactivation and maintain the mole ratio at a level that will stabilize the methane conversion at a particular level. This so-called induction period results in an initial loss of initiator activity and, hence, a lower level of conversion than if hydrogen had been present initially. To avoid this undesirable loss of conversion, it is preferred to add extraneous hydrogen to the reaction zone initially to minimize or prevent the initial loss of initiator activity and methane conversion. This extraneous hydrogen may be pure or in a mixture with other gases (e.g. as from a naphtha reformer) and may be added to the reaction zone separately or in mixture with the feed stream.

The conversion process of this invention can be practiced at any convenient temperature, including ambient conditions. The subject process has the advantage that pressures of one atmosphere or greater can be employed. Pressures of from about 10 torr to 15 atm preferably about 1 to about 2 atm are suitable. The relative amounts of acetylene and ethylene, which are the primary unsaturated products formed will vary with pressure, with a greater amount of ethylene being formed at elevated pressures (i.e., pressures greater than atmospheric). In addition to acetylene and ethylene, this invention also contemplates the formation of aromatic compounds such as benzene, alkyl benzenes, xylenes, and the like.

This invention will be further understood by reference to the following Examples which are not intended to restrict the scope of the appended claims.

EXAMPLE 1

Conversion of Methane Using Continuous Wave Microwave Radiation

A methane/hydrogen mixture (1:4 mole ratio) flowing at 75 ml/min (milliliters/minute) at atmospheric pressure was contacted with 0.37 g of a straight tungsten wire (approximately 0.76 mm in diameter and cut into about 47 mm lengths) in a reactor fabricated from a straight piece of quartz tubing, 7 mm in internal diameter. The part of the tube containing the wire was inserted in a WR430 microwave waveguide and positioned approximately one-quarter wavelength from a short circuit plate. The reactor was then irradiated with continuous microwave radiation centered at a 2.45 GHz frequency, with an average power of 10.0 watts. The methane conversion was calculated to be 4.8% using the following equation:

$$\% \text{ Methane Conversion} = \left[ 1 - \frac{\text{wt. \% methane in the products}}{\text{wt. \% methane in the feed}} \right] \times 100$$

After about 30 minutes the primary hydrocarbon products formed were acetylene (an average of 0.89 wt. %), and ethylene (an average of 0.68 wt. %). The product stream also contained a hydrogen (an average of 34.6 wt. % versus 33.3 wt. % in the mixture fed to the reactor), and small amounts of other higher hydrocarbons. The product stream contained methane (an average of 63.5 wt. % versus 66.7 wt. % in the mixture fed to the reactor).

EXAMPLE 2

Effect of Water on the Conversion of Methane Using Continuous Wave Microwave Radiation A methane/hydrogen mixture (1:4 mole ratio) containing 1.2 wt. % water and having a flow rate of 75 ml/min (milliliters/minute) at atmospheric pressure was contacted with 0.37 g of a straight tungsten wire (approximately 0.76 mm in diameter and cut into about 47 mm lengths) in a reactor as described in Example 1. The reactor was then irradiated with continuous microwave radiation centered at a 2.45 GHz frequency, with an average power of 9.8 watts. The methane conversion was 10.5%.

After about 30 minutes the primary hydrocarbon products formed were acetylene (an average of 2.17 wt. %), and ethylene (an average of 1.8 wt. %). The product stream also contained carbon monoxide (an average of 0.18 wt. %) and water (an average of 1.1 wt. % versus 1.2 wt. % in the mixture fed to the reactor) in addition to hydrogen (an average of 34.8 wt. %) versus 32.9 wt. % in the mixture fed to the reactor), and small amounts of other higher hydrocarbons. The product stream contained methane (an average of 59.0 wt. % versus 66.7 wt. % in the mixture fed to the reactor).

In comparing Examples 1 and 2, adding water to the methane/hydrogen reaction mixture results in about a 120% increase in methane conversion under continuous microwave radiation conditions. The methane conversion process generates reactive species which can react to form unsaturated hydrocarbon products.

EXAMPLE 3

Conversion of Methane Using Pulsed Microwave Radiation

A methane/hydrogen mixture (1:4 mole ratio) flowing at 75 ml/min (milliliters/minute) at atmospheric pressure was contacted with 0.37 g of a straight tungsten wire (approximately 0.76 mm in diameter and cut into about 47 mm lengths) in a reactor fabricated from a straight piece of quartz tubing, 7 mm in internal diameter. The part of the tube containing the wire was inserted in a WR430 microwave waveguide and positioned approximately one-quarter wavelength from a short circuit plate. The reactor was then irradiated with microwave radiation centered at a 2.45 GHz frequency and pulsed in an on/off cycle (0.07 seconds on in a total of 0.73 seconds) with an average power of 10.2 watts. The methane conversion was 12.6%.

After about 30 minutes the primary hydrocarbon products formed were acetylene (an average of 4.71 wt. %), and ethylene (an average of 0.97 wt. %). The product stream also contained hydrogen (an average of 35.7 wt. % versus 33.1 wt. % in the mixture fed to the reactor), and small amounts of other higher hydrocarbons. The product stream contained methane (an average of 58.5 wt. % versus 66.9 wt. % in the mixture fed to the reactor).

EXAMPLE 4

Effect of Water on the Conversion of Methane Using Pulsed Microwave Radiation

A methane/hydrogen mixture (1:4 mole ratio) containing 0.3 wt. % water and having a flow rate of 75 ml/min (milliliters/minute) at atmospheric pressures was contacted with 0.37 g of a straight tungsten wire (approximately 0.76 mm in diameter and cut into about 47 mm lengths) in a reactor as described in Example 1. The reactor was then irradiated with microwave radiation centered at a 2.45 GHz frequency and pulsed in an on/off cycle (0.07 seconds on in a total of 0.73 seconds) with an average power of 0.56 watts. The methane conversion was 57.1%.

After about 30 minutes the primary hydrocarbon products formed were acetylene (an average of 23.98 wt. %) and ethylene (an average of 4.42 wt. %). The product stream also contained carbon monoxide (an average of 0.17 wt. %) and water (an average of 0.17 wt. % versus 0.3 wt. % in the mixture fed to the reactor) in addition to hydrogen (an average of 42.3 wt. % versus 33.0 wt. % in the mixture fed to the reactor), and small amounts of other higher hydrocarbons. The product stream contained methane (an average of 28.6 wt. % versus 66.7 wt. % in the mixture fed to the reactor).

In comparing Examples 3 and 4, adding water to the methane/hydrogen reaction mixture results in about a 450% increase in methane conversion under pulsed microwave radiation conditions. In Examples 1 to 4, methane is used as the $C_{1+}$ hydrocarbon in the feed stream. However, other $C_{1+}$ hydrocarbons such as ethane, butane and the like may be employed in the feed stream.

EXAMPLE 5

Conversion of Methane Using Pulsed Microwave Radiation

A methane/hydrogen mixture (1:4 mole ratio) flowing at 25 ml/min (milliliters/min) at atmospheric pressure was contacted with 1.5 gm of tungsten wire (about 0.03 inches in diameter and cut into 45 mm lengths) in a reactor fabricated from WR430 waveguide bounded by quartz plate glass windows and positioned approximately one-quarter waveguide wavelength from a short circuit plate. The reactor was irradiated with microwave radiation centered at a 2.45 GHz frequency and pulsed in an on/off cycle (0.14 seconds on in a total of 3.5 seconds) with an average power of 3.6 watts. Methane conversion was calculated according to the following equation:

$$\% \text{ Methane Conversion} = \left[ 1 - \frac{\text{wt. \% methane in the products}}{\text{wt. \% methane in the feed}} \right] \times 100$$

The methane conversion obtained is shown in FIG. 1 as a function of time. FIG. 1 also shows that the primary hydrocarbon products produced were acetylene (an average of 33.6 wt. %) and ethylene (an average of 5.6 wt. %). Hydrogen (an average of 6.1 wt. %) and small amount of ethane (an average of 0.25 wt. %) were also produced.

EXAMPLE 6

Effect of $CH_4/H_2$ Mole Ratio on Methane Conversion

Figure 2:
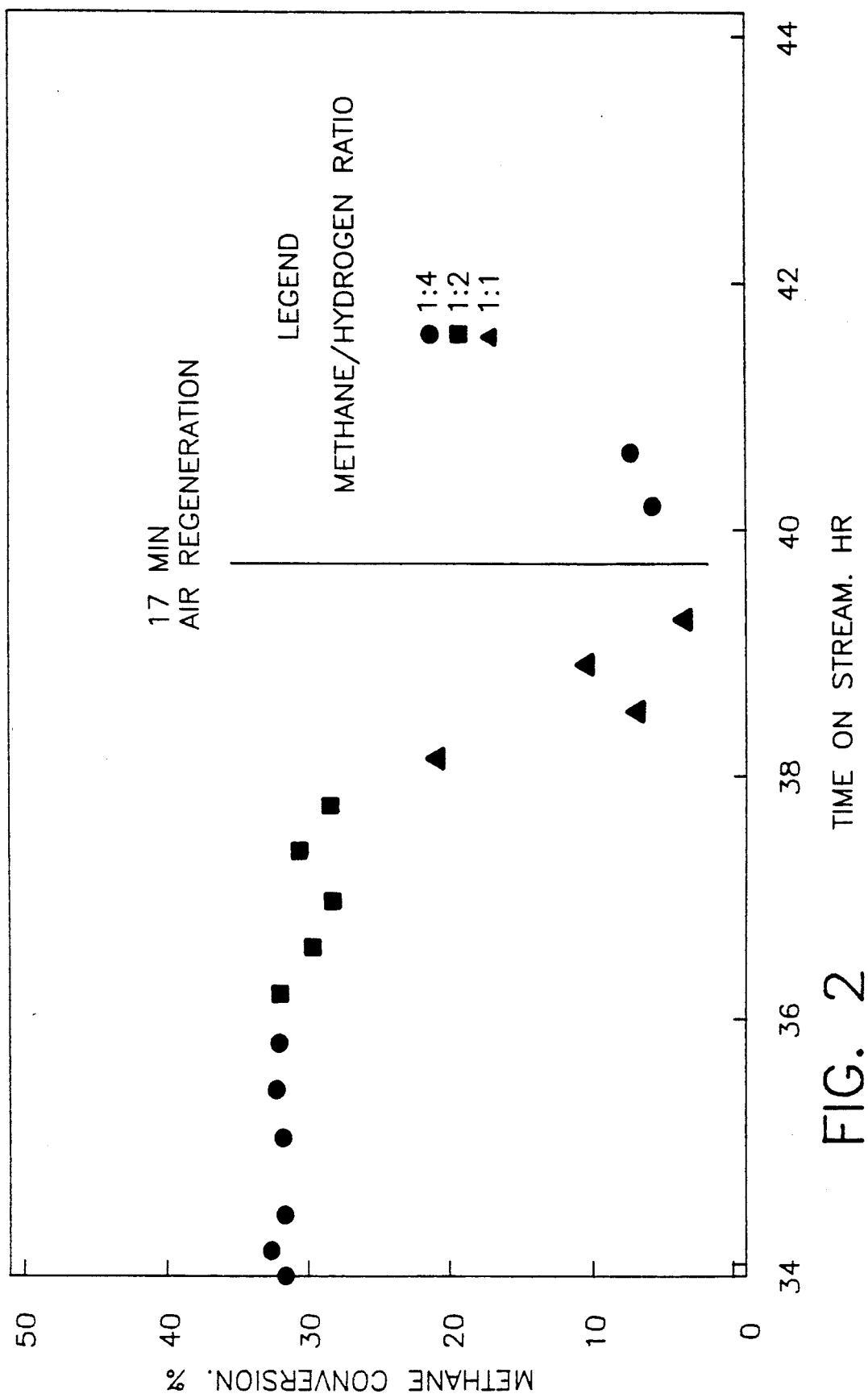
FIG. 2 is a graph of methane conversion versus time which shows the effect of $CH_4/H_2$ mole ratio on methane conversion.

Using the apparatus and procedure of Example 5 (except that 2.9 gm of iron wire was used and the average power ranged from 7.5 to 10 watts), the methane/hydrogen mole ratio was decreased from 1:4 to 1:1. The results of this test (as illustrated in FIG. 2) show that a reduction of the methane/hydrogen mole ratio from 1:4 to 1:2 had little effect on methane conversion. However, a further reduction to 1:1 resulted in a significant decrease in methane conversion. This decrease proved to be irreversible as shown by the further contact with the methane/hydrogen mixture (1:4 mole ratio) following 17 minutes of regeneration in air.

EXAMPLE 7

Effect of Various Plasma Initiators on Methane Conversion

Figure 3:
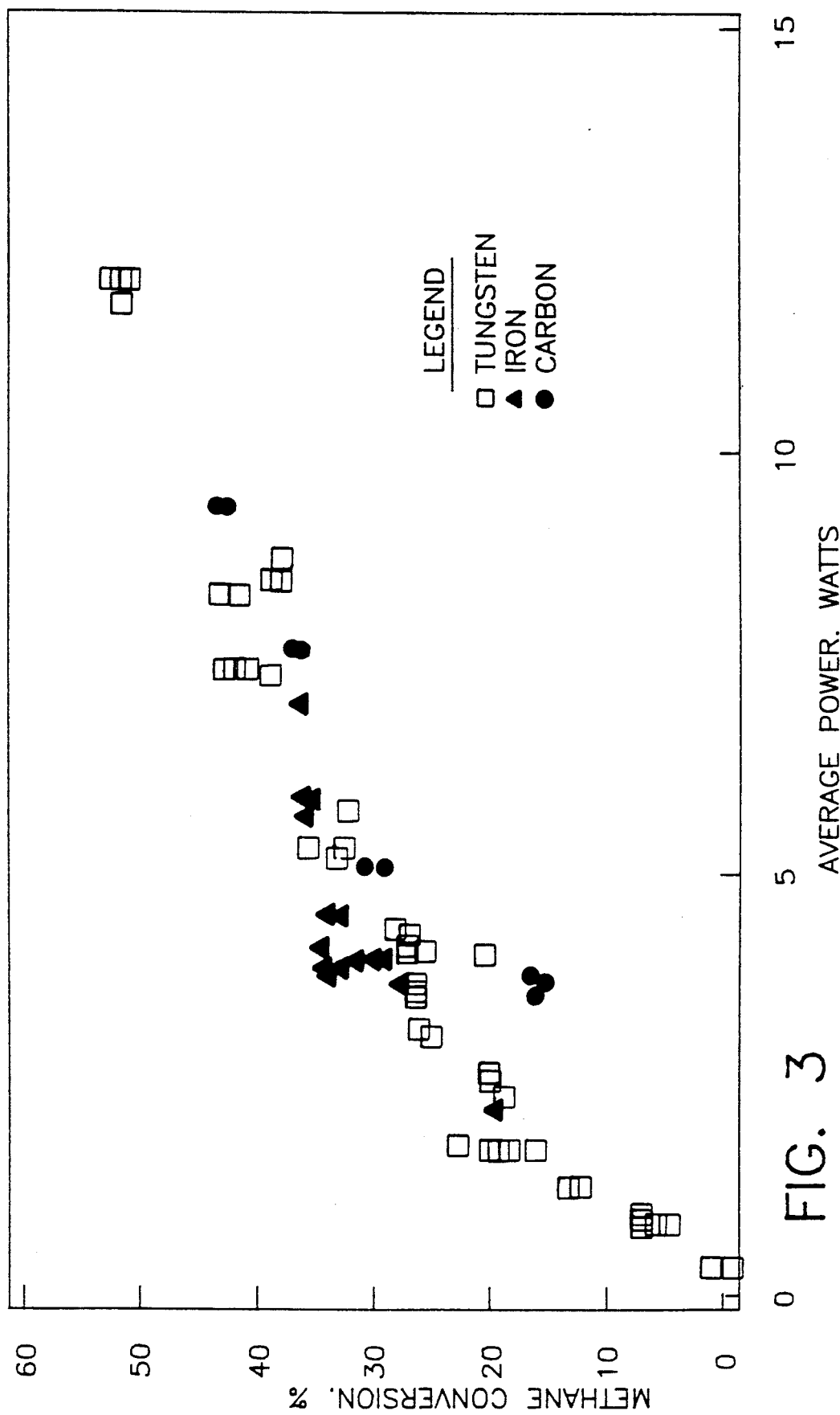
FIG. 3 is a graph of methane conversion versus average power which shows that various plasma initiators are effective for methane conversion.

Using the apparatus and procedure of Example 5, various plasma initiators were tested for their effectiveness in converting methane. The results of these tests (as illustrated in FIG. 3) show that tungsten, iron, or carbon (in the form of fibers) can be used without any adverse effect on methane conversion. However, in a companion experiment using silica fibers as the plasma initiator, no methane conversion was obtained.

EXAMPLE 8

Effect of Elevated Pressure on Product Distribution

Figure 4:
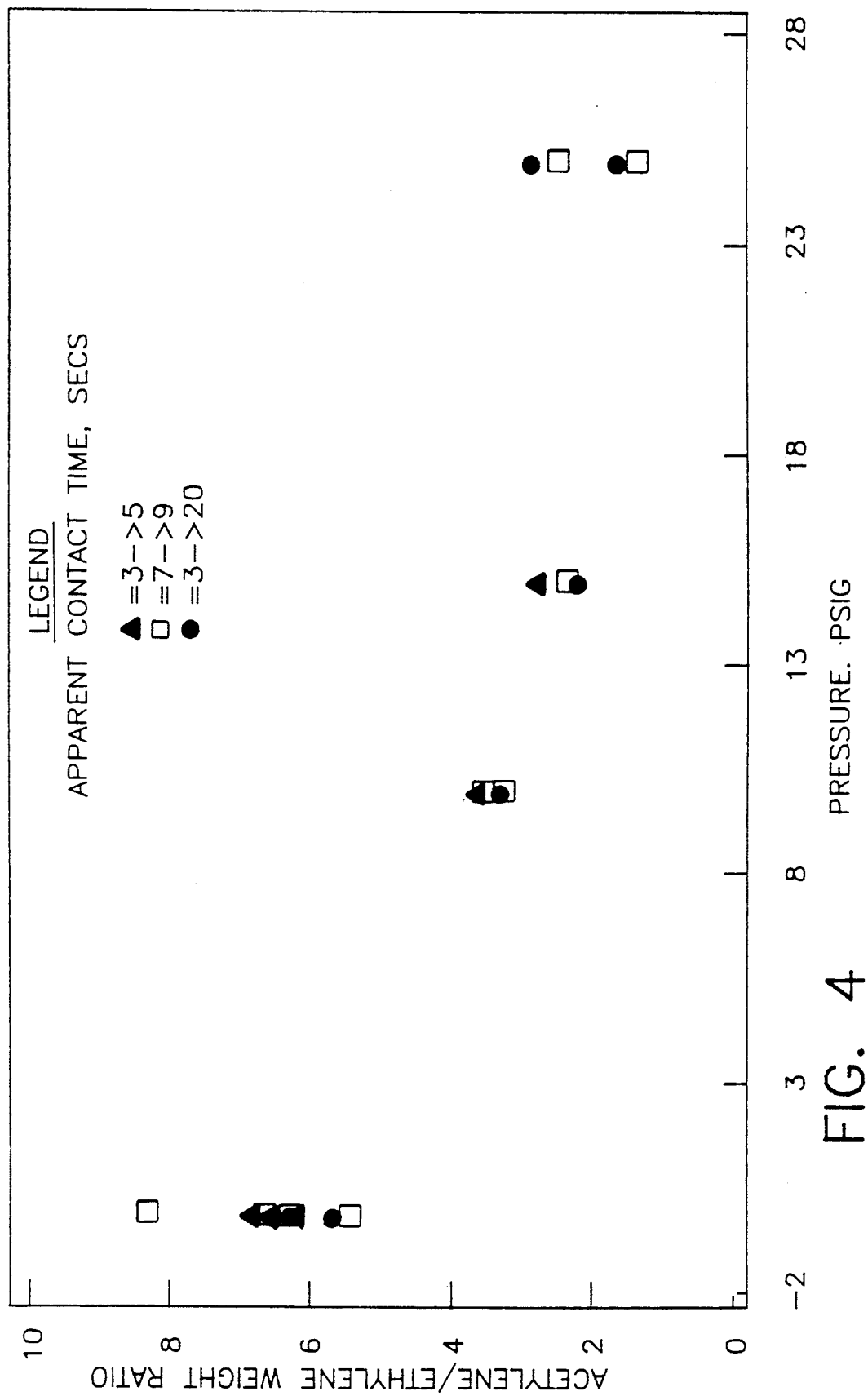
FIG. 4 is a graph of acetylene/ethylene weight ratio versus pressure which shows the effect of elevated pressure on product distribution.

Using the apparatus and procedure of Example 5 (except that the methane/hydrogen mole ratio ranged from 1:1 to 1:11 and methane flow rates ranged from 5 to 20 ml/min), tests were made to determine the effect of pressure on product selectivity. The results of these tests are shown in FIG. 4 at various apparent contact times, which is defined as follows:

Apparent Contact Time (sec) =

$$\frac{3600 \times FMW \times P}{1206 \times T \times CD \times WHSV \times (H_2:Feed) + 1)}$$

where
- FMW = Average molecular weight of the hydrocarbon feed
- P = Pressure, psia
- T = Arbitrarily set at 373° K.
- CD = Initiator bulk density, g/cc
- $H_2$:Feed = Hydrogen to methane mole ratio
- WHSV = Weight hourly space velocity, w/w/h
- 3600 = Conversion from hours to seconds
- 1206 = Gas constant in $(cm^3)(psia)/(gm\ mole)(° K.)$.

The data in FIG. 4 show that the product distribution is relatively insensitive to apparent contact time, but increasing pressure favors the formation of ethylene rather than acetylene. Thus, this invention also contemplates the products from methane conversion being primarily ethylene and hydrogen at elevated pressures.

EXAMPLE 9

Effect of Plasma Initiator Proximity on Methane Conversion

Figure 5:
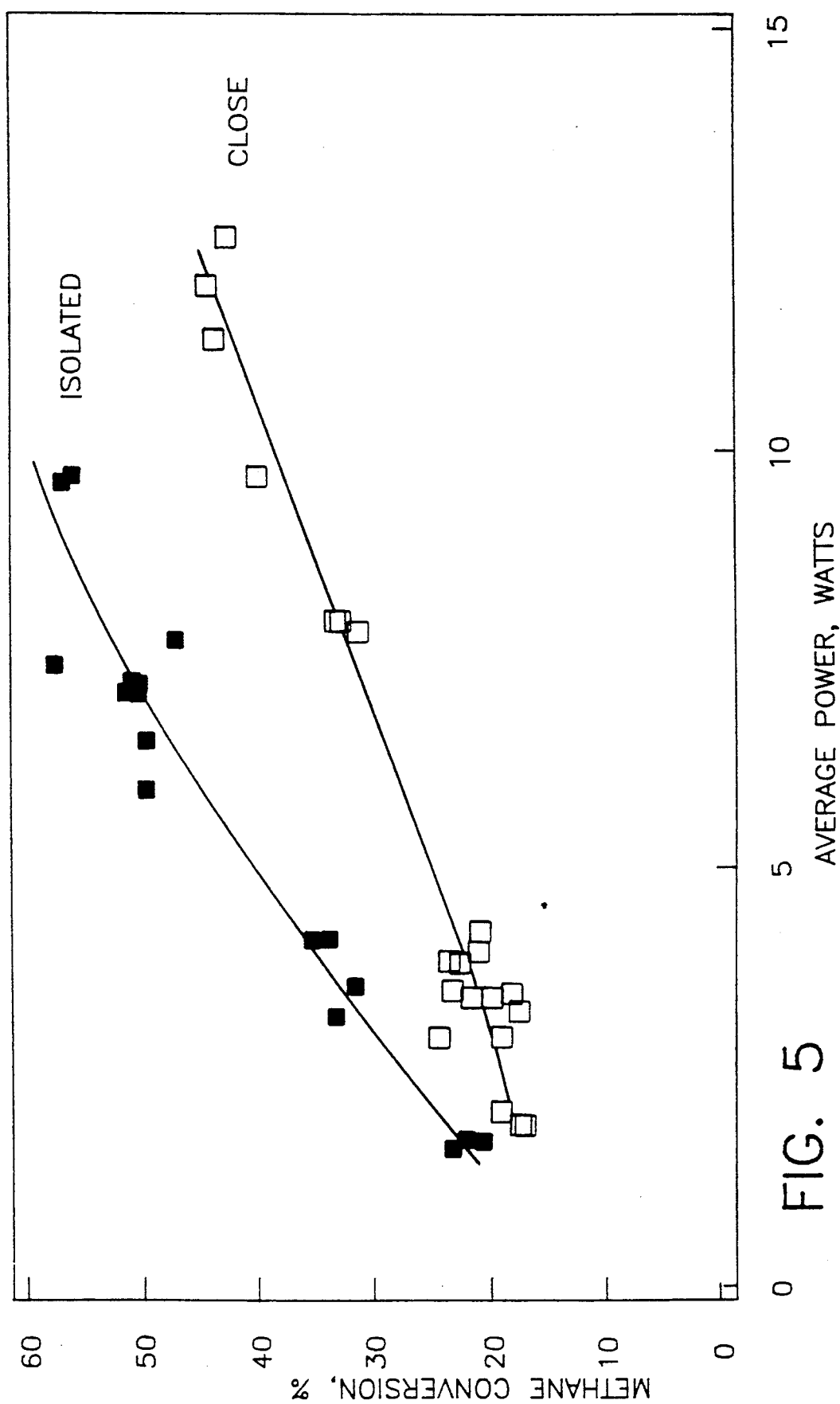
FIG. 5 is a graph of methane conversion versus average power which shows that the proximity of the plasma initiators affects methane conversion.

The apparatus and procedure of Example 5 was used to determine the effect of the proximity (or interpoint distance) of plasma initiators on methane conversion. In this example, the distance between plasma initiators was varied from about 0.5 cm (close) to about 1.0 cm (isolated). The results obtained (as illustrated FIG. 5) show that increased methane conversion is obtained when the initiators are isolated.

EXAMPLE 10

Metal Powders and Filings are Ineffective for Methane Conversion

A methane/hydrogen (1:4.2 mole ratio) mixture flowing at 12.9 ml/min at about atmospheric pressure was introduced into a quartz reactor and contacted with 0.2 g of nickel powder (from Alpha Products) having a 1.0 micron particle size. The reactor was irradiated with microwave radiation centered at 2.45 GHz frequency having 700 watts of power pulsed in an 50/50 on/off cycle, the cycle length of which was about 22 sec. The product stream was analyzed by gas chromatography and showed essentially no conversion of methane to acetylene and ethylene.

Following the same procedure, another experiment using a methane/hydrogen (1:4.1 mole ratio) mixture flowing at 11.2 ml/min and iron powder (Fisher I 60 grade) gave the same result.

Another experiment using 0.4 g iron filings (about 40 mesh) and the same conditions as the iron powder again gave the same result.

The data in this example show that metal powders and filings are ineffective initiators for methane conversion.

EXAMPLE 11

Effect of Number of Plasma Initiators on Methane Conversion

Figure 6:
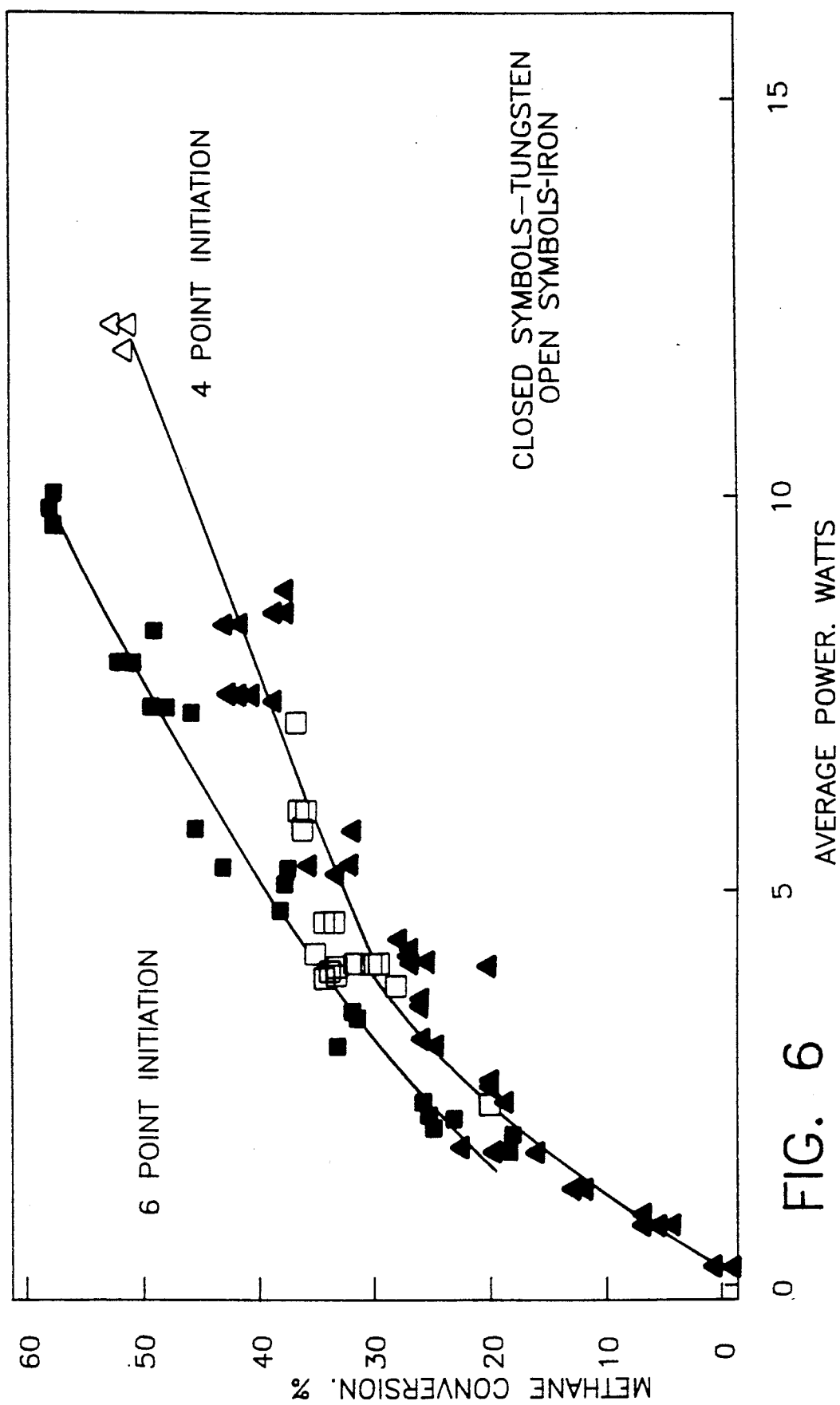
FIG. 6 is a graph of methane conversion versus average power which shows the effect of the number of plasma initiators on methane conversion.

The apparatus and procedure of Example 1 was used to determine the effect of the number of plasma initiators on methane conversion, except that 3.0 g of tungsten wire was used. The results obtained (as illustrated in FIG. 6) show that higher methane conversion is obtained with 6 rather than 4 plasma initiators.

What is claimed is:

1. A method for converting $C_{1+}$ hydrocarbons to primarily unsaturated hydrocarbons and hydrogen which comprises:
   (a) introducing into a reaction zone containing at least one plasma initiator capable of initiating an electric discharge in an electromagnetic field, a feed stream wherein the feed stream contains
      (1) at least one $C_{1+}$ hydrocarbon,
      (2) from about 0.02 to about 20 wt. % of water, based on the feed stream, and
      (3) molecular hydrogen in an amount sufficient to prevent deactivation of the plasma initiator; and
   (b) subjecting the reaction zone to microwave radiation for a period of time sufficient to convert at least a portion of the $C_{1+}$ hydrocarbon to primarily unsaturated hydrocarbons and hydrogen.

2. The method of claim 1 wherein the feed stream contains hydrogen in an amount sufficient to maintain activity of the plasma initiator.

3. The method of claim I wherein the feed stream pressure is from about 10 torr to about 15 atm.

4. The method of claim 1 wherein the plasma initiator is a metal, a non-metal other than silica or a composite of metal and non-metal.

5. The method of claim 4 wherein the metal is tungsten, iron, nickel, copper, their alloys, or mixtures thereof.

6. The method of claim 5 wherein the metal is tungsten or iron.

7. The method of claim 4 wherein the non-metal is calcium aluminate, carbon, iron oxide, or mixtures thereof.

8. The method of claim I wherein the primarily unsaturated hydrocarbons are $C_2$–$C_3$ unsaturated hydrocarbons.

9. The method of claim 1 wherein a plurality of plasma initiators are present in the reaction zone.

10. The method of claim 1 where the frequency of the microwave radiation is at least 0.3 GHz.

11. The method of claim I wherein the amount of water is from about 0.1 to about 5 wt. %.

12. The method of claim 8 wherein the $C_2$–$C_3$ unsaturated hydrocarbons are ethylene and acetylene.

13. The method of claim 3 wherein the pressure is from about 1 atm to about 2 atm.

* * * * *